United States Patent [19]

Toy et al.

[11] 3,962,323

[45] June 8, 1976

[54] PROCESS FOR PREPARING ALKYL- OR ARYL-PHOSPHONOTHIOIC DIHALIDES

[75] Inventors: Arthur D. F. Toy, Stamford, Conn.; Eugene H. Uhing, Ridgewood, N.J.

[73] Assignee: Stauffer Chemical Company, Westport, Conn.

[22] Filed: Nov. 14, 1974

[21] Appl. No.: 523,761

[52] U.S. Cl. .............................. 260/543 P; 260/961; 260/999
[51] Int. Cl.² ......................................... C07F 9/42
[58] Field of Search ............................... 260/543 P

[56] References Cited
UNITED STATES PATENTS

| | | | |
|---|---|---|---|
| 3,461,189 | 8/1969 | Nagel | 260/543 P X |
| 3,803,226 | 4/1974 | Uhing et al. | 260/543 P |

OTHER PUBLICATIONS

B368,128; Jan., 1975; Froment et al.

*Primary Examiner*—Ethel G. Love
*Attorney, Agent, or Firm*—William R. Robinson

[57] ABSTRACT

Alkyl- or arylphosphonothioic dihalides are prepared by contacting a reactant selected from the group consisting of mono-alkyl or aryl mercapto phosphorothionodihalidate, dialkyl or aryl mercapto phosphorothionohalidate or tri- alkyl or aryl tetrathiophosphate with phosphorus trihalide under at least autogenous pressure at a temperature of from about 200°C. to about 400°C. The compounds obtained are useful as constituents in insecticides, fungicides and pharmaceuticals, and as intermediates in preparation of other organophosphorus compounds.

5 Claims, No Drawings

PROCESS FOR PREPARING ALKYL- OR ARYL-PHOSPHONOTHIOIC DIHALIDES

The present invention relates to a new and improved process for the preparation of alkyl- or arylphosphonothioic dihalides.

BACKGROUND OF THE INVENTION

Alkylphosphonothioic dihalides have been prepared in the prior art by reacting alkyl halides with phosphorus trihalides in the presence of aluminum chloride, followed by sulfurization of the reaction product. The alkyl halidephosphorus trihalide reaction proceeds at room temperature according to the formula set forth in Heuben-Weyl, Methoden der Organis Chenchemie at vol. 12, part 1 (1965) at p. 396:

$$XR—CL + PCl_3 + AlCl_3 \rightarrow XR—PCl_4 \cdot AlCl_3 \quad (1)$$

The Heuben-Weyl reference also notes that the reaction has been attempted in the absence of the aluminum chloride catalyst with little success. The reaction has the disadvantage that one mole of aluminum chloride is lost for each mole of product prepared.

The reaction product must be sulfurized to obtain the phosphonothioic dihalide product. A. M. Kinnear and E. A. Perren, Journal Chem. Soc., 3437 (1952) showed that $(EtPCl_3)(AlCl_4)$ can be sulfurized with $H_2S$. It gave a yield of only 32% $EtP(S)Cl_2$ while obtaining a 47% yield of a by-product $EtPS_2$.

Alkyl or arylphosphonothioic dihalides also can be prepared according to our U.S. Pat. No. 3,790,629 by reacting an aliphatic or aromatic hydrocarbon with a pentavalent thiophosphorous compound having at least two halogens attached thereto under at least autogenous pressure at a temperature of from 200°C. to 450°C. Also see "Journal of the American Chemical Society", 88:13, July 5, 1966 ". . . A New Synthesis of Phosphonothioic Dihalides," Baker et al, p. 3041.

Cycloalkanephosphonothioic dichlorides have also been prepared by reacting a cycloalkane with thiophosphoryl chloride under irradiation with mercury lamps. Reaction times are long and low yields are reported (Angrew. Chem. Internat. Edit., vol. 9 (1970), No. 6 at p. 458).

THE INVENTION

In accordance with the present invention there is provided a new method for preparing compounds of the formula:

 (II)

wherein R is hydrocarbyl including groups selected from $C_1$-$C_{20}$ alkyl; cycloalkyl of 4–6 carbons in the ring and the $C_1$-$C_4$ alkyl substituted derivatives thereof; aralkyl of up to 2 fused rings, the alkyl portion having from 1 to 20 carbons; aryl of up to 3 fused rings and the $C_1$-$C_4$ alkyl substituted derivatives thereof; or biphenyl and the $C_1$-$C_4$ alkyl substituted derivatives thereof, and X is a halogen such as chlorine or bromine.

Exemplary R groups of the alkyl type are methyl, ethyl, n-propyl, isopropyl, n-butyl, isobutyl, tert-butyl, pentyl, hexyl, heptyl, octyl, nonyl, decyl, dodecyl, tetradecyl, hexadecyl, octadecyl, and eicosyl. Aralkyl R groups include phenylmethyl, phenylethyl, phenylbutyl, phenyloctyl, phenylhexadecyl, and the corresponding naphthyl derivatives. Cycloalkyls such as cyclohexyl and cyclopentyl and the $C_1$-$C_4$ alkyl substituted derivatives thereof also are included. Typical aryl-type R groups are phenyl, methylphenyl, i.e. tolyl, ethylphenyl, propylphenyl, butylphenyl, naphthyl, methylnaphthyl, ethylnaphthyl, propylnaphthyl, butylnaphthyl, anthryl, methylanthryl, propylanthryl, butylanthryl, and disubstituted forms such as dimethylphenyl, dimethylnaphthyl, diethylanthryl, and the like.

The method comprises contacting a reactant selected from the group consisting of mono-alkyl or aryl mercapto phosphorothionodihalidate, di- alkyl or aryl mercapto phosphorothionohalidate, or tri- alkyl or aryl tetrathiophosphate of the structural formulas:

 (III)

or

 (IV)

or

 (V)

with phosphorus trihalide. Wherein R and X are as defined above, with the proviso that the R groups in structural formulas IV and V can be the same or different.

The following equations (1), (2) and (3) are representative of the reaction wherein reactant III is used, the reaction wherein reactant IV is used and the reaction wherein reactant V is used, respectively.

$$RSP(S)X_2 + PX_3 \rightarrow RP(S)X_2 + P(S)X_3 \quad (1)$$
$$(RS)_2P(S)X + 2PX_3 \rightarrow 2RP(S)X_2 + P(S)X_3 \quad (2)$$
$$(RS)_3PS + 3PX_3 \rightarrow 3RP(S)X_2 + P(S)X_3 \quad (3)$$

A general reaction scheme illustrating the foregoing reactions is as follows:

$(RS)_aP(S)X_b + aPX_3 \rightarrow aRP(S)X_2 + P(S)X_3$ where: $a+b=3$; $a=1$, 2 or 3; $b=0$, 1 or 2.

It is not necessary to utilize reactants in the process of the present invention in stoichiometric amounts, however, byproduct formation can be minimized if stoichiometry is followed. The mono- or di- alkyl or aryl mercapto phosphorothionochloridate reactants can be prepared in accordance with the disclosure in our U.S. Patent No. 3,879,500 The tri- alkyl or aryl tetrathiophosphates can be prepared in accordance with known processes.

The process of the present invention is carried out at an elevated temperature and at least at autogenous pressure. Temperatures of from about 200°C. to about 400°C. can be used though temperatures of about 250°C. to about 325°C. are generally employed. The process of the present invention requires no separate catalyst in order to effect reaction. The dihalide products are known and have utility as chemical intermediates--particularly, in the preparation of insecticides, fungicides, pharmaceuticals, and other organophosphorus compounds.

The method of the present invention can conveniently be effected by introducing the individual reactants into a reaction zone capable of withstanding elevated pressure, such as a metal bomb autoclave, or other pressure vessel, and carrying out the reaction under at least the autogenous pressure developed by the reactants at the reaction temperature. Pressures of up to 200 atmospheres above the autogenous pressure can also be used but are less desirable due to the inconvenience of requiring a pressurization system. The time of reaction may vary over relatively wide limits such as between about 1 to 30 hours depending upon reaction temperature and the particular R group. For example, if R is methyl, a higher temperature and a longer reaction time would be required in comparison to the case wherein R is a longer chain hydrocarbon group. The preferred reaction time has been found to be between about 2 to 20 hours.

In general, the reaction equipment should include a pressure vessel. The vessel should be equipped with an agitation means (a rocker, vibrator, or stirrer) for best results.

The reaction can be carried out in a continuous or batchwise system as desired.

The products of the reaction are purified by conventional methods such as by fractional distillation of liquids and crystallization or extraction of solid products.

The identification of products is achieved by conventional methods, such as elemental analysis and gas chromatography for purity, and mass spectrometer and $^{31}$P-nmr, $^{1}$H-nmr, and infrared analysis to establish structure.

Illustrative of the compounds which can be prepared by the method of the present invention are:

CH$_3$P(S)Cl$_2$
C$_2$H$_5$P(S)Cl$_2$
C$_3$H$_7$P(S)Cl$_2$
C$_4$H$_9$P(S)Cl$_2$
C$_5$H$_{11}$P(S)Cl$_2$
(CH$_3$)$_3$C—CH$_2$P(S)Cl$_2$
C$_8$H$_{17}$P(S)Cl$_2$
C$_{18}$H$_{37}$P(S)Cl$_2$
C$_{18}$H$_{37}$P(S)Br$_2$

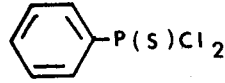

CH$_3$P(S)Br$_2$
C$_2$H$_5$P(S)Br$_2$
C$_3$H$_7$P(S)Br$_2$
C$_4$H$_9$P(S)Br$_2$
C$_5$H$_{11}$P(S)Br$_2$
(CH$_3$)$_3$C—CH$_2$P(S)Br$_2$
C$_8$H$_{17}$P(S)Br$_2$

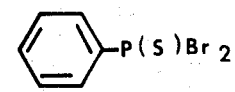

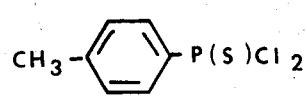

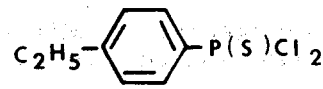

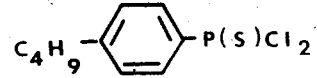

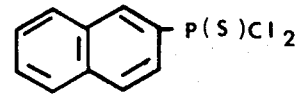

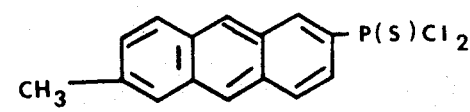

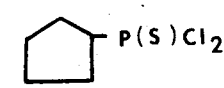

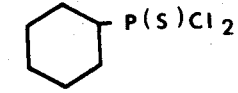

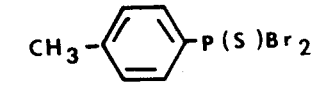

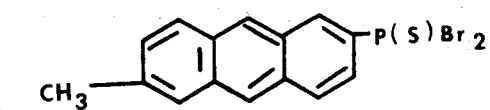

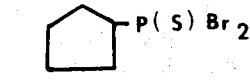

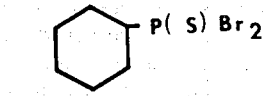

The products of the present invention, being dihalides of pentavalent thiophosphorus, can be subject to all the known reactions which such compounds undergo. The compounds of the invention can be used as intermediates to make insecticides as illustrated by the process for making O-ethyl s-phenyl ethylphosphonothioate according to the following illustrative reaction scheme:

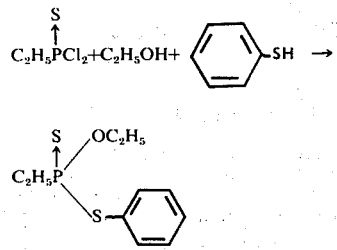

The sodium salts of the acids can also be prepared. Other uses would be obvious to one skilled in the art.

The present invention will be more fully illustrated in the examples which follow.

EXAMPLE 1

Preparation of methylphosphonothioic dichloride:

$$CH_3SP(S)Cl_2 + PCl_3 \rightarrow CH_3P(S)Cl_2 + P(S)Cl_3$$

A stock solution was made by mixing 1.5029 g. $CH_3SP(S)Cl_2$ (0.0083 mole) and 1.452 g. $PCl_3$ (0.00835 mole). A 0.85-ml. sample was placed in a 4-ml. Carius tube and sealed. The tube was placed in a 300-ml. autoclave rated at 5,000 psig. along with 50-ml. benzene to equalize the pressure. The autoclave was heated at 305°C for 14 hours. After cooling the tube was removed and opened. The liquid was analyzed by glc. and $^1$H-nmr.

| Component | Wt. % |
|---|---|
| $PCl_3$ | 21 |
| $P(S)Cl_3$ | 27 |
| $CH_3P(S)Cl_2$ | 41.7 |
| $CH_3SP(S)Cl_2$ | 4.5 |
| $(CH_3)_2P(S)Cl$ | 1.0 |
| Unknown | 4.8 |

After standing, a small amount of solid precipitate formed ($P_4S_3$ to $P_4S_7$).

$^1$H-nmr mole % analysis for $CH_3$ groups shows that 98% of the starting methyl groups can be accounted for.

| $^1$H-nmr Analysis for $CH_3$ Groups | |
|---|---|
| Component | Mole % |
| $CH_3P(S)Cl_2$ | 87 |
| $CH_3SP(S)Cl_2$ | 8 |
| $(CH_3)_2P(S)Cl$ | 3 |
| Unknown | 2 |

EXAMPLE 2

$$(CH_3S)_2P(S)Cl + 2PCl_3 \rightarrow 2CH_3P(S)Cl_2 + PSCl_3$$

A stock solution of 1.1030 g. $(CH_3S)_2P(S)Cl$ (0.00574 mole and 1.6015 g. $PCl_3$ (0.01169 mole) was made. A 0.085 ml. sample was placed in an autoclave as described in Example 1 and heated to 300°C. for 12 hours. After cooling, the tube was opened and the liquid was analyzed by glc. and $^1$H-nmr.

| glc. Analysis | |
|---|---|
| Component | Wt. % |
| $PCl_3$ | 18 |
| $P(S)Cl_3$ | 16.8 |
| $CH_3P(S)Cl_2$ | 53 |
| $CH_3SP(S)Cl_2$ | 6 |
| $(CH_3)_2P(S)Cl$ | 3 |
| Unknown | 3.2 |

A small amount of yellow precipitate was present in the liquid.

Based on $^1$H-nmr mole % analysis for $CH_3$ groups, all of the starting methyl groups were accounted for.

| $^1$H-nmr Analysis for $CH_3$ Groups | |
|---|---|
| Component | Mole % |
| $CH_3P(S)Cl_2$ | 88 |
| $(CH_3)_2P(S)Cl$ | 6 |
| $CH_3SP(S)Cl_2$ | 6 |

EXAMPLE 3

$$(CH_3S)_3PS + 3PCl_3 \rightarrow 3CH_3P(S)Cl_2 + P(S)Cl_3$$

In a 4 ml. Carius tube was placed 0.51 grams $(CH_3S)_3$ (0.0025 mole) and 1.02 grams $PCl_3$(0.0075 moles). After sealing, the Carius tube was placed in an autoclave as described in Example 1. The autoclave was heated at 300°C. for 12 hours. After cooling, the tube was removed from the autoclave and opened. The tube contained a small amount of solid material (about 0.1 gram) and 1.2 grams liquid. Analysis by glc gives the following result:

| glc Analysis | |
|---|---|
| Component | Weight % |
| $PCl_3$ | 11 |
| $P(S)Cl_3$ | 10 |
| $CH_3P(S)Cl_2$ | 68 |
| $(CH_3)_2P(S)Cl$ | 7 |
| $CH_3SP(S)Cl_2$ | 3 |
| Unknown | 1 |

Based on $^1$H-nmr mole percent analysis for $CH_3$ groups, 98.2% of the starting methyl groups were accounted for.

| $^1$H-nmr Analysis for $CH_3$ Groups | |
|---|---|
| Component | Mole % |
| $CH_3P(S)Cl_2$ | 88 |
| $(CH_3)_2P(S)Cl$ | 7.1 |
| $CH_3SP(S)Cl_2$ | 3.1 |
| Unknown | 1.8 |

EXAMPLE 4

$$(C_2H_5S)_3PS + 3PCl_3 \rightarrow 3C_2H_5P(S)Cl_2 + P(S)Cl_3$$

In a 3 ml. Carius tube were placed 0.8996 grams $(C_2H_5S)_3PS$ (0.0036 mole) and 1.49 grams $PCl_3$ (0.011 mole). After sealing, the Carius tube was placed in an autoclave as described in Example 1. The autoclave was heated at 300°C. for 12 hours. Analysis by $^{31}P$-nmr gave the following results:

| Chemical Shift from $H_3PO_4$ (ppm) | $^{31}P$-nmr Analysis Compound | Mole % |
| --- | --- | --- |
| −219 | $PCl_3$ | 16 |
| −94.4 | $C_2H_5P(S)Cl_2$ | 56 |
| −79.6 | Unknown | 23 |
| −31.4 | $P(S)Cl_3$ | 4 |

EXAMPLE 5

$(C_4H_9S)_3PS + 3 PCl_3 \rightarrow 3C_4H_9P(S)Cl_2 + P(S)Cl_3$

In a 3 ml. Carius tube were placed 0.9014 grams of crude $(C_4H_9S)_3PS$ (0.0027 mole) and 1.11 grams $PCl_3$ (0.008 mole). The tube was placed in an autoclave as described in Example 1 and was heated at 270°C. for 12 hours. The crude product was analyzed by $^{31}P$-nmr which gave the following results:

| Chemical Shift from $H_3PO_4$ (ppm) | Compound | Mole % |
| --- | --- | --- |
| −91.7 | $C_4H_9P(S)Cl_2$ | 11 |
| −219 | $PCl_3$ | 45.8 |

Under these conditions the reaction had not gone to completion.

EXAMPLE 6

$(C_8H_{17}S)_3PS + 3PCl_3 \rightarrow 3C_8H_{17}P(S)Cl_2 + P(S)Cl_3$

In a 3 ml. Carius tube were placed 0.8326 grams crude $(C_8H_{17}S)_3PS$ (0.00167 mole) and 0.7876 grams $PCl_3$ (0.0057 mole). The tube was placed in an autoclave as described in Example 1 and was heated at 250°C. for 12 hours. Analysis by $^{31}P$-nmr showed that 12 mole % $C_8H_{17}PSCl_2$ (chemical shift = −91.1 ppm) had formed under these conditions.

EXAMPLE 7

$(CH_3S)_3PS + 3PBr_3 \rightarrow 3CH_3P(S)Br_2 + P(S)Br_3$

In a 3 ml. Carius tube were placed 0.6502 grams $(CH_3S)_3PS$ (0.00318 mole) and 2.79 grams $PBr_3$ (0.01 mole). The tube was placed in an autoclave as described in Example 1 and was heated at 250°C. for 8 hours. The product was analyzed by $^1H$-nmr and gave the following results:

| Chemical Shift (δ) | Compound Assignment | Mole % (Based on $CH_3$ area) |
| --- | --- | --- |
| 3.3 | $CH_3P(S)Br_2$ | 72 |
| 2.78 | $CH_3SP(S)Br_2$ | 15 |
| 2.55 | $(CH_3)_2P(S)Br$ | 13 |

Some unreacted $PBr_3$ and $P(S)Br_3$ were also present.

EXAMPLE 8

$CH_3SP(S)Br_2 + PBr_3 \rightarrow CH_3P(S)Br_2 + P(S)Br_3$

In a 3 ml. Carius tube were placed 0.987 grams of a composition (60% $CH_3SP(S)Br_2$ and 40% $(CH_3S)_2P(S)Br$) and 1.61 grams $PBr_3$. The tube was placed in an autoclave as described in Example 1 and was heated at 250°C. for 8 hours. Analysis of the crude product by $^1H$-nmr gave the following results:

| Chemical Shift (δ) | Compound Assignment | Mole % (Based on $CH_3$ area) |
| --- | --- | --- |
| 3.3 | $CH_3P(S)Br_2$ | 61 |
| 2.78 | $CH_3SP(S)Br_2$ | 34 |
| 2.55 | $(CH_3)_2P(S)Br$ | 5 |

Some $PBr_3$ and $P(S)Br_3$ were also present.

EXAMPLE 9

$(CH_3S)_2P(S)Br + 2PBr_3 \rightarrow 2CH_3P(S)Br_2 + P(S)Br_3$

In a 3 ml. Carius tube were placed 0.896 grams of a mixture (86% $(CH_3S)_2P(S)Br$ and 14% $CH_3SP(S)Br_2$) and 2.046 grams $PBr_3$. The tube was placed in an autoclave as in Example 1 and was heated at 250°C. for 8 hours. The product was analyzed by $^1H$-nmr and gave the following results:

| Chemical Shift (δ) | Compound Assignment | Mole % (Based on $CH_3$ area) |
| --- | --- | --- |
| 3.3 | $CH_3P(S)Br_2$ | 67 |
| 2.78 | $CH_3SP(S)Br_2$ | 24 |
| 2.55 | $(CH_3)_2P(S)Br$ | 7 | some $PBr_3$ and $P(S)Br_3$ were also present.

The present invention is defined in the claims which follow.

What is claimed is:

1. A method of preparing compounds of the formula:

$$R-P\overset{\overset{S}{\uparrow}}{\underset{X}{\diagdown}}X \quad (II)$$

wherein R is selected from the group consisting of $C_1$-$C_{10}$ alkyl; cycloalkyl of 4 – 6 carbons in the ring and the $C_1$-$C_4$ alkyl substituted derivatives thereof; aralkyl of up to 2 fused rings, the alkyl portion having from 1 to 20 carbon atoms; aryl of up to 3 fused rings and the $C_1$-$C_4$ alkyl substituted derivatives thereof; or biphenyl and the $C_1$-$C_4$ alkyl substituted derivatives thereof and X is selected from the group consisting of chlorine or bromine, comprising contacting under at least an autogenous pressure at a temperature of from about 200°C. to about 400°C. a reactant selected from the group consisting of compounds of the structural formulas:

$$RS\overset{\overset{S}{\uparrow}}{P}-X_2 \quad (III)$$

or $$(RS)_2\overset{\overset{S}{\uparrow}}{P}-X \quad (IV)$$

or

(V)

wherein R and X are as defined above, with phosphorus trihalide.

2. The method of claim 1 wherein the hydrocarbon radicals R in structural formulas IV and V are the same or different.

3. The method of claim 2 wherein R is selected from the group consisting of methyl, ethyl, n-propyl, isopropyl, n-butyl, isobutyl, tert-butyl, pentyl, hexyl, heptyl, octyl, nonyl, decyl, dodecyl, tetradecyl, hexadecyl, octadecyl and eicosyl.

4. The method of claim 2 wherein R is selected from the group consisting of phenylmethyl, phenylethyl, phenylbutyl, phenyloctyl, phenylhexadecyl and the corresponding nephthyl derivatives.

5. The method of claim 2 wherein R is selected from the group consisting of phenyl, methylphenyl, ethylphenyl, propylphenyl, butylphenyl, naphthyl, methylnaphthyl, ethylnaphthyl, propylnaphthyl, butylnaphthyl, anthryl, methylanthryl, propylanthryl, butylanthryl, dimethylphenyl, dimethylnaphthyl and diethylanthryl.

* * * * *